United States Patent [19]

Buchta et al.

[11] 4,042,733

[45] Aug. 16, 1977

[54] FORMING SOLID, ADHESIVE-FREE COMPOSITE OF MEMBRANE FILTERS AND CELLULOSIC CARDBOARD

[75] Inventors: Karl Buchta; Mohamed Abdou, both of Ingelheim am Rhein; Harald Woltersdorf, Konigslutter, all of Germany

[73] Assignee: Boehringer Ingelheim GmbH, Ingelheim am Rhein, Germany

[21] Appl. No.: 689,792

[22] Filed: May 25, 1976

Related U.S. Application Data

[63] Continuation of Ser. No. 592,184, July 1, 1975, abandoned.

[30] Foreign Application Priority Data

July 4, 1974 Germany .............................. 2432049

[51] Int. Cl.$^2$ ................................ B05D 3/02
[52] U.S. Cl. ......................................... 427/391; 427/2; 428/304; 428/411; 428/477; 428/478; 428/514; 428/533; 252/316; 424/36; 424/37; 195/1; 195/54; 95/57
[58] Field of Search .............. 428/411, 476, 477, 514, 428/533, 304; 427/391

[56] References Cited

U.S. PATENT DOCUMENTS

| | | | |
|---|---|---|---|
| 1,987,930 | 1/1935 | Goessmann | 428/477 |
| 3,052,237 | 9/1962 | Chand | 428/533 X |
| 3,535,194 | 10/1970 | Demme et al. | 428/304 X |
| 3,914,524 | 10/1975 | Monte | 428/533 |

OTHER PUBLICATIONS

Derwent Pub., Ltd., 70960u, Germany, DT-2320946-Q, Aug. 11, 1973, Miles Labs., Inc.
Derwent Pub., Ltd., 54696v 30, Dutch, NL 7400-336, May 7, 1974, C. H. Boehringer Sonn.

*Primary Examiner*—P. C. Ives
*Attorney, Agent, or Firm*—Hammond & Littell

[57] ABSTRACT

A solid, adhesive-free, layered composite material consisting of two clearly defined layers, one made of membrane filters and the other of porous material, the said composite material being formed by bringing a polymeric membrane filter forming substance in its gel condition into contact with the porous material, and solidifying the said gel on the porous material; the composite material is useful as a nutrient medium carrier for microbiological tests.

5 Claims, No Drawings

FORMING SOLID, ADHESIVE-FREE COMPOSITE OF MEMBRANE FILTERS AND CELLULOSIC CARDBOARD

This is a continuation of copending Ser. No. 592,184, filed July 1, 1975, now abandoned.

This invention relates to a novel composite material of membrane filters and porous material, to a process for the production of said composite material, as well as to its use as a carrier for nutrient media for microbiological examinations.

BACKGROUND OF THE INVENTION

Membrane filters of graded permeability are produced according to various methods and from various materials. They consists, for example, of a thin film derived from colloidal solutions, such as gelatin, collodium, silicic acid, cellulose ester or cellulose, which, upon evaporating and coagulating, form a lattice work the cavities of which form a sponge-like structure. Depending upon the production method, the cross-sections of the pores may vary greatly, so that for example bacteria and even particles up to molecular size may be screened off.

In general, membrane filters have to be supported in use; larger ones mostly on sieve-plates or frits, because by themselves they are not sufficiently strong to withstand mechanical stress.

For many purposes a solid composite material made of membrane filter and a porous backing would be very desirable, which completely preserves the individual properties of the membrane filter on the one hand and the properties of the porous backing on the other hand.

It is known to use an adhesive for pasting the membrane filter on a porous backing, but this method has the disadvantage that the adhesive may influence in an unpredictable manner the properties of the system membrane filter/porous backing. It is also known to impregnate a porous backing with a solution which forms a membrane filter upon drying, so that the membrane layer forms at least partially within the porous material. But the product thus formed has properties other than those of the individual components. This defect applies especially to the surface, which no longer exhibits the smooth membrane filter surface required for many types of work, but takes on the structure of the porous backing.

If the backing consists of a porous material which has been soaked in nutrient media and dried, for example a cardboard disc which is meant to be used for differentiated bacteriological inhibition tests, a membrane filter is required adjacent to the porous backing. In this case it is not practicable to produce a composite material either by pasting the two components together, or by impregnating the porous material with the membrane filter forming component, because the layer of adhesive influences the diffusion of the nutrients between porous backing and membrane filter in an unpredictable manner and, moreover, the absence of the pure, smooth membrane surface prevents the formation of, for example, concentric inhibition circles in the test for antibiotic efficacy.

OBJECTS OF THE INVENTION

It is an object of this invention to provide a composite material consisting of a membrane filter and a porous backing which completely retains the properties of both the components and avoids the disadvantages of the prior art.

THE INVENTION

Such a composite material is obtained by bringing a membrane filter produced from polymeric substances in contact with the porous backing during gelatinizing of the polymeric membrane former, and solidifying the latter on the porous backing. The composite material thus obtained makes it possible to perform not only qualitative, but also quantitative determinations in bacteriological inhibition tests.

According to a particular embodiment of this invention, such a composite material is produced as follows:

A solution capable of membrane formation is spread in known manner on a continuous, highly polished belt. Suitable membrane formers are, in particular, cellulos nitrate, cellulose acetate, gelatin, PVC, PVA, polyamide or alginate.

The applied solution is passed through certain climatic zones with the aid of the moving belt, for example, as described in German Patent No. 1,017,596. During this process the solvents evaporate, and a solid substance in the form of a porous, flat material, namely the membrane filter, is formed on the belt. Between the solution stage and the solid membrane filter stage, the membrane-forming material passes a stage in which the polymeric membrane-forming agent is present as a gel.

If during this phase, especially between onset of syneresis and final solidification of the membrane filter which is recognizable by the appearance of an ice flowerlike texture in the membrane film, a porous backing, such as a cardboard ribbon, is carefully brought into contact with this gel, the membrane filter which is subsequently formed adheres firmly to the porous material and solidifies on the same. After the production process is finished, the membrane filter as well as the porous backing form a composite material, but each component is clearly recognizable in its former, unmodified form. This feature is primarily exhibited by the completely perfect surface of the membrane. In analogous fashion, a second membrane may be applied to the other side of the porous material.

The adhesion of one component of the composite material to the other is very good, and in the absence of exterior force no separation of the porous backing from the membrane filter will take place. The adhesion may be effected more or less firmly, as desired, depending upon whether the contact between the porous material and membrane-forming gel is effected more at the beginning or toward the end of the gel phase of the membrane-forming material.

The composite material of membrane filter and porous material according to the invention, especially cardboard of about 1 to 2 mm thickness, is particularly well suited for use in microbiological tests in which the formation of clearly defined, circular inhibition zones is required or desired. For the purpose the composite material is impregnated with a conventional nutrient for microorganisms, and it thus essentially assumes the function of such agents as agar-agar or gelatin, which are generally used for solidification of nutrient medium substrates.

After sterilization, the impregnated composite material (nutrient cardboard) may be used immediately for microbiological test purposes. However, it is also possible to dry the impregnated composite material, cut it into suitable shapes, such as circular discs and to store the same in sterilized condition and in sterile packaging. Whenever desired, a nutrient medium may be produced quickly by moistening the dry, sterile composite material with sterile water, which can then be used in the conventional manner. The nutrient cardboards on which colonies of microorganisms have been grown may, if desired, be dried after staining, and after covering them with a foil they can be kept as permanent records.

The advantages of the composite material according to this invention show themselves particularly in those microbiolgical tests, where a standardization of the test is made possible by reproducible properties of the nutrient medium; this is especially successful if synthetic nutrient media are used, that is nutrient media composed of finite compounds, instead of the usually employed mixtures of substances (peptones, meat extracts, yeast extracts and further additives.

Such a synthetic nutrient medium may be composed as follows:

| Solution I: | |
|---|---|
| Components | gm/liter*) |
| L-Arginine | 0.523 |
| L-Asparaginic acid | 1.065 |
| L-Cysteine | 0.485 |
| L-Glutaminic acid | 2.207 |
| Glycocoll | 0.15 |
| L-Histadine | 0.31 |
| L-Leucine | 0.787 |
| L-Isoleucine | 0.525 |
| L-Lysine | 0.585 |
| L-Methionine | 0.298 |
| L-Phenylalanine | 0.33 |
| L-Proline | 0.345 |
| L-Threonine | 0.357 |
| L-Tryptophane | 0.102 |
| L-Tyrosine | 0.362 |
| L-Valine | 1.17 |
| Sodium chloride | 2.92 |
| Potassium chloride | 0.298 |
| Anhydrous sodium acetate | 0.984 |
| Sodium pyruvate | 1.1 |
| Sodium glycerophosphate . 5 $H_2O$ | 5.2 |
| Mg $SO_4$ . 7 $H_2O$ | 0.049 |
| Adenine | 0.009 |
| Guanine | 0.009 |
| Uracil | 0.011 |
| Aqua dist. | 950.0 ml |
| Solution II: | |
| Components | gm/liter*) |
| D-Glucose | 1.98 |
| Inosite | 0.011 |
| Choline-Cl | 0.014 |
| Nicotinic acid amide | 0.011 |
| Thiamin-HCl | 0.01 |
| Riboflavin | 0.001 |
| Pyridoxin-HCl | 0.006 |
| Pantothenic acid calcium salt | 0.01 |
| Folic acid | 0.009 |
| Biotin | 0.0002 |
| Na-Glycerophosphate . 5 $H_2O$ | 1.04 |
| p-Nitrophenyl propanetriol | 0.005 |
| Pimaricin | 0.30 |
| Aqua dist. | 50.0 ml |
| Solution III: | |
| 10% aqueous sodium hydroxide solution | |

*)The indicated volumetric quantities refer to the total amount of distilled water used for preparing solutions I and II, that is, in the present example 950 ml plus 50 ml.

*The indicated volumetric quantities refer to the total amount of distilled water used for preparing solutions I and II, that is, in the present example 950 ml plus 50 ml.

PREPARATION:

1. The ingredients of solution I are dissolved in 950 ml of distilled water, and the solution is sterilized in an autoclave at 121° C. for 20 minutes.
2. The glucose, vitamins and growth promoters for solution II are dissolved in 50 ml of distilled water, and the solution is disinfected by sterile filtering through membrane filters, pore size 0.22 μm.
3. The 10% sodium hydroxide solution is sterilized in an autoclave for 20 minutes at 121° C. 4. Solution I and II are each heated to 55° C and then admixed; with the aid of solution III the pH-value of the mixed solution is adjusted to 7.2, at 47° C.

The amounts of the components for solutions I and II may be varied; for example, the amounts may be reduced by one-half or they may be doubled, based on the amounts indicated above. However, in general, it is not advantageous to omit a component, such as an amino acid, completely or to alter the pH-value of the mixture substantially. The use of these media for a standardized test is only possible if the deviation does not significantly affect the growth of the microorganisms and thus the size of the inhibition zones formed in the test.

The test may be carried out in the following way:

The composite material impregnated with the nutrient medium (circular disc of corresponding diameter) is put into a Petri-dish with the membrane filter side up and is inoculated with a predetermined quantity of the microorganism sample to be tested (optionally after dilution). Then, filterpaper discs about 4 mm in diameter, which have been charged with predetermined quantities of antimicrobially active substances (antibiotics, sulfonamides) are placed on the membrane filter surface, and the Petridish is incubated for 16 to 24 hours at a given temperature.(such as 36 ± 1° C).

Given a definite charge of antimicrobially active substance on the filterpaper discs and a microorganism growth density which can be determined in the usual way, there is a connection between the inhibition zone diameter and the minimal inhibition concentration of the antimicrobially active substance in question. On the other hand, the maximum attainable or therapeutically admissible blood level for conventional antimicrobially substances is known. Therefore, it is possible to estimate the therapeutic efficacy of an antimicrobially active substance, based on the diameter of the inhibition zone.

If the test is carried out with a standardized nutrient solution under standardized conditions, reproducible results are obtained with the acid of the composite material according to the invention. By means of known, comparable devices, for example, with a membrane-linked cardboard box, as described in German Offenlegungsschrift No. 2,320,946, this has not been possible. A further test in which the nutrient cardboards according to the invention can be used with special advantage is described in German Offenlegungschrift No. 2,301,211 or published Dutch Application 74/00336.

While the present invention has been illustrated with aid of certain specific embodiments thereof, it will be readily apparent to others skilled in the art that the invention is not limited to these particular embodiments, and that various changes and modification may be made without departing from the spirit of the invention or the scope of the appended claims.

We claim:

1. The method of forming a solid, adhesive-free, layered composite material composed of two clearly defined layers consisting of a membrane filter layer and a porous backing layer, comprising the steps of depositing on cellulosic cardboard a layer of a gelatinized polymeric membrane-forming substance between onset of synerisis and final solidification thereof, and allowing said membrane-forming substance to solidify on said cellulosic cardboard.

2. The method of claim 1, where said polymeric membrane-forming substance is cellulose nitrite, cellulose acetate, gelatin, polyvinylchloride, polyvinylacetate, a polyamide or an alginate.

3. The method of claim 1, where said cellulosic cardboard is impregnated with a nutrient solution for microorganisms.

4. The method of claim 3, where said impregnated cellulosic cardboard is dried.

5. The method of claim 3, where said nutrient solution is an aqueous solution which contains about 0.25 to 1 gm of L-arginine, 0.5 to 2 gm of L-asparginic acid, 0.25 to 1 gm of L-crysteine, 1 to 4 gm of L-glutaminic acid, 0.1 to 0.4 gm glycocoll, 0.15 to 0.6 gm of L-histidine, 0.4 to 1.6 gm of L-leucine, 0.25 to 1 gm of L-isoleucine, 0.3 to 1.2 gm of L-lysine, 0.15 to 0.6 gm of L-methionine, 0.15 to 0.6 gm of L-phenylalanine, 0.2 to 0.8 gm of L-proline, 0.2 to 0.8 gm of L-threonine, 0.05 to 0.2 gm of tryptophane, 0.2 to 0.8 gm of L-tyrosine, 0.5 to 2 gm of L-valine, 1.5 to 6 gm of sodium chloride, 0.15 to 0.6 gm of potassium chloride, 0.5 to 2 gm of anhydrous sodium acetate, 0.5 to 2 gm of sodium pyruvate, 3 to 12 gm of sodium glycerophosphate pentahydrate, 0.025 to 0.1 gm of magnesium sulfate heptahydrate, 0.005 to 0.02 gm of adenine, 0.005 to 0.02 gm of guanine, 0.005 to 0.02 gm of uracil, 1 to 4 gm of D-glucose, 0.005 to 0.02 gm of inosite, 0.005 to 0.02 gm of choline chloride, 0.005 to 0.02 gm of nicotinic acid, 0.005 to 0.02 gm of thiamine hydrochloride, 0.0005 to 0.0002 gm of riboflavin, 0.003 to 0.012 gm of pyridoxin hydrochloride, 0.005 to 0.02 gm of calcium pantothenate, 0.005 to 0.02 gm of folic acid, 0.0001 0.0004 gm of biotin, 0.0025 to 0.01 gm of p-nitrophenylpropanetriol, 0.05 to 0.4 gm of pimaricin per liter of water, as well as the required quantity of sodium hydroxide in dilute aqueous solution for adjustment of the pH to 7.2.

* * * * *